United States Patent [19]

Furuta

[11] Patent Number: 6,156,525
[45] Date of Patent: *Dec. 5, 2000

[54] **METHOD FOR JUDGING ERADICATION OF *H. PYLORI* BASED ON RATES OF CHANGES IN THE PEPSINOGEN I/II RATIO**

[76] Inventor: Takahisa Furuta, 181-2-506, Aoicho, Hamamatsu-shi, Shizuoka 433, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/536,102

[22] Filed: Sep. 29, 1995

[30] Foreign Application Priority Data

Aug. 28, 1995 [JP] Japan ................................. 7-240418

[51] Int. Cl.[7] ................................................. G01N 33/573
[52] U.S. Cl. ............................................. 435/7.4; 435/7.1
[58] Field of Search ................................................. 435/7.4

[56] References Cited

U.S. PATENT DOCUMENTS 4,830,010   5/1989   Marshall ................................. 128/630

OTHER PUBLICATIONS

Hunter et al., "Serum Pepsinogens as Markers of Response to Therapy *Helicobacter pylori* Gastritis", Digestive Diseases and Sciences, vol. 38, No. 11, pp. 2081–2086, Nov. 1993.

Asaka et al., "The Role of *Helicobacter pylori* in Peptic Ulcer Disease", Gastroenterol Jpn., vol. 28, Suppl. 5, pp. 163–167, 1993.

Chittajallu et al., "Effect of *Helicobacter pylori* on Serum Pepsinogen I and Plasma Gastrin in Duodenal Ulcer Patients", Scand J. Gastroenterol, vol. 27, pp. 20–24, 1992.

Rauws et al., "*Campylobacter pyloridis*–Associated Chronic Active Antral Gastritis", Gastroenterology, vol. 94, No. 1, pp. 33–49, 1988.

Ichinose et al., "Radioimmunoassay of Serum Group I and Group II Pepsinogens in Normal Controls and Patients with Various Disorders", Clinica Chimica Acta., vol. 126, pp. 183–191, 1982.

Samloff et al., "Relationships Among Serum Pepsinogen I, Serum Pepsinogen II, and Gastric Mucosal Histology", Gastroenterology, vol. 83, No. 1. pp. 204–209, Jul. 1982.

Fraser, A.G. et al, Aliment. Pharmacol. Ther., 1992, vol. 6(3), p. 389–94.

Plebani, M et al, Lancet, vol. 340, Jul. 4, 1992, pp. 51–52.

Karnes, W.E. et al, Gastroenter., 1991, vol. 101(1), p. 167–174.

Nakata, H. et al, J. Clin. Gastroenterol., 1995, vol. 20 (Sup. 2), p. S118–20.

Chang, FY et al, Curr. Therap. Res., vol. 56(9), Sep. 1995, p. 887–893.

Asaka, M. et al, Gastroent, 1992, vol. 102(3), p. 760–766.

(List continued on next page.)

*Primary Examiner*—James C. Housel
*Assistant Examiner*—Ginny Allen Portner
*Attorney, Agent, or Firm*—Wenderoth, Lind & Ponack, L.L.P.

[57] ABSTRACT

A method of judging the eradication of *H. pylori* to judge whether the sample is positive or negative through a quick and easily operation is provided. A PG I value and a PG II value in the body fluids (e.g., in the blood) of an *H. pylori* positive patient are measured before the *H. pylori* eradicating treatment and after the passage of a period in which a substantially significant result occurs from the eradicating treatment, a PG I/PG II ratio in the body fluids (e.g., in the blood) is found, a rate of change in the PG I/PG II ratio in the body fluids (e.g., in the blood) is found before the *H. pylori* eradicating treatment and after the passage of the period in which a substantially significant result occurs from the eradicating treatment, and the change in the PG I/PG II ratio is used as a marker to indicate that *H. pylori* is eradicated.

9 Claims, 7 Drawing Sheets

RELATIONSHIPS AMONG THE SERUM PEPSINOGEN I / II RATIO BEFORE THE ERADICATION TREATMENT AND RATES OF CHANGES IN THE PEPSINOGEN I / II RATIO BEFORE AND AFTER THE ERADICATION TREATMENT DEPENDING UPON SUCCESS OR FAILURE OF Helicobacter pylori ERADICATION

OTHER PUBLICATIONS

Biasco, G et al, J. Clin Patnol., Sep. 1993, vol. 46(9) p. 826–8.

Ivey, KJ, J. Gastrolentol. Hepatol., 1994, vol. 9 (Suppl 1), p. 5109–11.

Fukuda, H. et al, Jpn. J. Cancer. Res., vol. 86(1), p. 64–71, Jan. 1995.

Schlemper, R.J. et al, Gut, 1995, vol. 37(2), p. 199–204.

Parente, F. et al, Gut, 1995, vol. 37(2), p. 210–215.

Dotto, P et al, Aug. 1995, Curr. Therp. Res., vol. 56(8), p. 777–786.

Furuta, T. et al, J. Clin. Gast., 1995, vol. 20 (Suppl. 2), 5107–111.

Plebani, M, Crit. Rev. Clin. Lab. Sci, 1993, vol. 30(3), p. 273–328.

Wagner, S. et al, Am. J. Gastroent., vol. 89(8), 1994, p. 1211–8.

Kato, I. et al, Int'l, J. of Cancer, 1995, vol. 62(5) p. 512–18.

Ashorn, M et al, Scad. J. Gastroenterol., Mar. 1994, vol. 29(3) p. 203–8.

Pilotto, A et al, Jun. 1996, vol. 44(6), p. 665–670, JAGS.

Aoyama et al (Apr. 1995), Gastroenterol, vol. 108(4), PA 47.

De Bona et al, 1994, Am. J. Gastroenterol., vol. 89(8) p. 1369.

Dotto et al (Aug. 1995), Current Therapeutic Res. vol. 55(8), p. 777–786.

Ferrana et al (Apr. 1995), Gastroenterol, vol. 108(4), PA93.

Wagner et al, 1994, Am. J. of Gastroenterol., vol. 89(8), p. 1211–1218.

Westerveld, B.D. et al, Cancer, vol. 59, Mar. 1, 1987, p. 952–958.

Di Mario et al (Jul. 1995), Gut, vol. 37(Suppl. 1), A57.

Fukuda et al (Jan. 1995), Japanese J. Cancer. Res., vol. 86(1), p. 64–71.

Schlemper et al (1995), Gut, vol. 37(2), p. 199–204.

Vianello et al (1994), Am. J. Gastroenterol., vol. 89(8) p. 1390.

Kato, I. et al, Int. J. Cancer, vol. 62(5), p. 512–518, 1995.

I Michael Samloff et al, Gastroenterol., 1982, vol. 83, p. 204–9.

Plebani, M., Crit. Rev. Clin. Lab. Sci., 1993, vol. 30(3), p. 273–328.

Hunter et al, 1993, vol. 38(11), Dig. Dis. and Science, p. 2081–2086.

FIG. 2

JUDGMENT OF ERADICATION BASED UPON VARIOUS METHODS OF DETECTING
Helicobacter pylori AND UPON RATES OF CHANGES IN THE SERUM PEPSINOGEN I / II RATIO

| JUDGING METHOD | SENSITIVITY | SPECIFICITY | VALIDITY |
|---|---|---|---|
| RAPID UREASE TEST | 80.0% | 100% | 88.9% |
| CULTURE TEST | 61.1% | 100% | 78.6% |
| RATE OF CHANGE IN PEPSINOGEN I / II RATIO | 97.7% | 96.4% | 96.9% | n = 98

FIG. 4

TRANSITION IN THE SERUM GASTRIN AND SERUM PEPSINOGEN VALUES
DEPENDING UPON ERADICATION AND NON-ERADICATION

METHOD FOR JUDGING ERADICATION OF H. PYLORI BASED ON RATES OF CHANGES IN THE PEPSINOGEN I/II RATIO

BACKGROUND OF THE INVENTION

1. Field of the Invention

The present invention relates to a method of judging eradication of *Helicobacter pylori* (*H. pylori*: Hp) which is considered to be one of the causes of gastric and duodenal disease by examining body fluids, such as blood samples to be tested. In recent years, furthermore, it has been suspected that *H. pylori* is associated with development of gastric cancer, The present invention relates to a method of quickly and easily judging if *H. pylori* still remains in a person infected with *H. pylori* after *H. pylori* eradicating therapy, by using body fluids such as blood samples. The invention is further related to a method of eradicating *H. Pylori* and to a method of treating gastric and duodenal ulcer by combining the above-mentioned method with a medicine which contains, as main active ingredients, a drug for suppressing gastric acid secretion and an antibiotic or an antibacterial agent.

2. Description of Related Art

In diagnosing the infection with *H. pylori*, it has been urged to develop a method of correctly measuring (diagnosing) the presence or absence (eradication) of *H. pylori* after *H. pylori* eradicating therapy. So far, the eradication of *H. pylori* has been judged relying upon bacterial culture, urease test and histopathological examination, which require the collection of samples by mucosal biopsy during gastroduodenoscopy, and detecting the bacteria based upon nucleic acids extracted from gastric biopsied samples or gastric juice by polymerase chain reaction (PCR) techniques. After the eradicating treatment, however, culture test and urease test exhibit decreased sensitivity, and false negative results often appear. In the microscopic analysis of tissues, furthermore, the sensitivity varies depending upon the degree of skill of pathological diagnosticians. Besides, the distribution of *H. pylori* in the stomach is not uniform. When the biopsied tissues are used as samples, therefore, *H. pylori* is not always contained in the biopsied tissues that are removed in a several number. Therefore, though infection with *H. pylori* should turn out to be positive, it often turns out to be false negative due to sampling error. The PCR method features a high sensitivity but permits false positive to appear due to dead bacteria or contaminated bacteria. Namely, the PCR is cumbersome and cannot be easily put into practice. Besides, these examinations noted above require endoscopic examination which is invasive and cannot be easily performed repetitively. Examination methods other than a PCR method have been widely employed, however, lacking sensitivity and leaving a high probability of developing false negative. The urea breath test does not require the endoscopic inspection. However, $^{13}$C-urea is expensive and, besides, an apparatus for measuring the mass of carbon dioxide including $^{13}$C (i.e., gas isotope ratio mass spectrometry) is very expensive, too. Only a small number of such machines exist in Japan accompanied by problem in economy and availability. It has been said that a drop in the anti-*H. pylori* titer in the blood works effectively for judging the eradication of *H. pylori*. Even when *H. pylori* is actually eradicated, however, a period of not shorter than half a year is required before the antibody titer decreases (e.g., the titer decreases after half a year to more than nine months have passed), leaving a problem in that the result is not quickly obtained. Most patients who are eradication-treated are usually shifted from inpatients who receive therapeutic treatment in a hospital into outpatients who receive therapeutic treatment by going to the hospital or who are examined by going to the hospital as their condition recover. In practice, however, very few people attend the hospital to get examined for more than half a year. It has therefore been urged to carry out the precise measurement within short periods of time. On the other hand, patients without eradication of *H. pylori* have great chances of developing diseases again such as gastric or duodenal ulcer and gastric cancer.

It has been desired to provide means for quickly judging the eradication of *H. pylori* by examining body fluids such as blood, which is an ordinarily employed-examination means, without using endoscopy, to objectively judge the eradication of *H. pylori* by simply utilizing a conventional examination device that has heretofore been widely used.

It has been known that pepsinogen is an inactive precursor of pepsin which is a proteolytic enzyme in the gastric juice, and turns into pepsin by removing a peptide at the N-terminal thereof. Immunologically, the pepsinogens can be classified into two groups of pepsinogen I (PG I) and pepsinogen II (PG II), and their distributions delicately differ depending upon the places in the living body. It has been known that the PG I value and the PG II value in the blood of patients infected with *H. pylori* are high and that these values decrease and the PG I/PG II ratios increase by eradication of *H. pylori* (Fred M. Hunter, et al., Digestive Dieases and Sciences, Vol. 38, No. 11, pp. 2081–2086, 1993). Since the basal values differ depending upon the individual patients, however, it is difficult, relying upon the value of serum pepsinogens, to determine whether eradication is accomplished or not. In practice, the PG I value in the blood and the PG II value in the blood vary depending upon the individual patients due to ages and environments in which they live. Besides, extension of atrophy of the stomach which affects pepsinogen values, not always corrected with age in every patients. Therefore, it is meaningless to use the measured values or to establish certain cut-off values.

SUMMARY OF THE INVENTION

In order to develop means for judging the eradication of *H. pylori* to quickly screen based upon a simple operation whether the sample is positive or negative, the present inventors have conducted keen study to find a method of correct measurement by utilizing body fluid PG I values such as blood PG I values and body fluid PG II values such as blood PG II values in samples to be tested. As a result, the inventors have succeeded in developing a simple method of judging the eradication of *H. pylori* maintaining good sensitivity and specificity by screening whether the sample is positive or negative.

The present invention provides a method of judging the eradication of *H. pylori* which comprises measuring a PG I value and a PG II value in the body fluids such as blood, from an *H. pylori* positive patient, before the *H. pylori* eradicating treatment and after the passage of a period in which a substantially significant result occurs from the eradicating treatment, finding a PG I/PG II ratio in the body fluids such as blood PG I/PG II ratio, finding a rate of change of the body fluid PG I/PG II ratio before the *H. pylori* eradicating treatment to the body fluid PG I/PG II ratio after the passage of the period in which a substantially significant result occurs from the eradicating treatment, and using the rate of change in the PG I/PG II ratio as a marker to indicate whether *H. pylori* is eradicated or not.

More preferably, the present invention provides a method of judging the eradication of *H. pylori*, wherein a rate of change in the PG I/PG II ratio in the body fluids, which is greater than rate of a predetermined value is used as a marker to indicate that *H. pylori* is eradicated, the change in the PG I/PG II ratio in the body fluids being measured before the *H. pylori* eradicating treatment and after the passage of the period in which a substantially significant result occurs from the eradicating treatment. The present invention further provides a method of judging the eradication of *H. pylori* by measuring a PG I value and a PG II value in the body fluids such as in the blood of an *H. pylori* positive patient before the *H. pylori* eradicating treatment and after the passage of a period in which a substantially significant result occurs from the eradicating treatment, finding a PG I/PG II ratio in the body fluids such as PG I/PG II ratio in the blood, finding a rate of the change in the PG I/PG II ratio in the body fluids before the *H. pylori* eradicating treatment and after the passage of the period in which a substantially significant result occurs from the eradicating treatment, and using the change in the ratio thereof which is greater than a predetermined value as a marker to indicate that *H. pylori* is eradicated, and setting the change in the ratio depending upon the PG I/PG II ratio in the body fluids such as the PG I/PG II ratio in the blood of before the *H. pylori* eradicating treatment,

DETAILED DESCRIPTION OF THE PREFERRED EMBODIMENTS

The present invention provides a method of measuring and judging whether *H. pylori* is eradicated or not by measuring a PG I value and a PG II value in various body fluids such as PG I value and PG II value in the blood sample before the *H. pylori* eradicating treatment and after the passage of a period in which a substantially significant results occurs from the eradicating treatment, finding a PG I/PG II ratio in the body fluids such as PG I/PG II ratio in the blood, finding a rate of the change in the PG I/PG II ratio in the body fluids such as in the PG I/PG II ratio in the blood before the *H. pylori* eradicating treatment and after the passage of the period in which a substantially significant result occurs from the eradicating treatment, and using the the rate of the change in the PG I/PG II ratio as a marker to indicate that *H. pylori* is substantially eradicated.

In a typical embodiment of the present invention, it is measured and judged whether *H. pylori* is eradicated or not by measuring a PG I value and a PG II value in various body fluids such as PG I value and PG II value in the blood samples before the *H. pylori* eradicating treatment and after the passage of a period in which a substantially significant result occurs from the eradicating treatment, finding a PG I/PG II ratio in the body fluids such as PG I/PG II ratio in the blood, finding a rate of the change in the PG I/PG II ratio in the body fluids such as PG I/PG II ratio in the blood before the *H. pylori* eradicating treatment and after the passage of the period in which a substantially significant result occurs from the eradicating treatment, and using the rate of the change in the ratio thereof which is greater than a predetermined value as a marker to indicate that *H. pylori* is substantially eradicated. According to the present invention, there is further provided a method of measuring and judging whether *H. pylori* is eradicated or not by the cut-off values of rates of the changes in the PG I/PG II ratios established according to the PG I/PG II ratios in the body fluids such as the PG I/PG II ratio in the blood of before the *H. pylori* eradicating treatment.

According to the present invention, furthermore, it allow one to eradicate *H. pylori* and to treat gastric and duodenal ulcer efficiently, quickly and reliably by combining the above-mentioned measuring method and judging method together with a pharmaceutical composition which chiefly comprises a drug for suppressing gastric acid secretion (e.g., proton pump inhibitor such as lansoprazole or omeprazole, or an $H_2$ blocker such as ranitidine or famotidine) and an antibiotic (e.g., amoxicillin or clarithromycin) or an anti-bacterial agent (e.g., metronidazole) and, further, containing a mucosa-defending factor (e.g., ecabet sodium, plaunotol or sofalcone). Examples of the proton pump inhibitor are activated lansoprazole, AG2000, AG1749, E3810, E3810 thioether, NC1300, etc. Examples of the $H_2$ blocker are further cimetidine, roxatidine, nizatidine, etc. but the $H_2$ blocker is limited thereto. It should be noted that any drug can be used for eradicating *H. pylori* and for treating gastric and duodenal ulcer provided it can be used without limitation in combination with the judging method of the present invention and provided it suppresses secretion of acid in the stomach, exhibits antibiotic property, antibacterial property or serves as a factor for defending mucosa.

Antibacterial treatment against *H. pylori* (eradicating treatment) was effected for an *H. pylori* positive patient suffering from peptic ulcer diseases. The endoscopic examination and blood-collecting examination were carried out before the treatment and one month after the treatment. Gastric mucosal biopsy was performed during gastroduodenoscopy, and the biopsied samples of gastric mucosa were subjected to culture test, histopathological examination and urease test. Gastric mucus was subjected to the PCR to detect *H. pylori*. The judgment of eradication of *H. pylori* was achieved on the basis that every result of the culture test, urease test, histopathological examination and PCR analysis throughout the observation period. A blood sample was collected before the antibacterial treatment of *H. pylori* and one month after the end of antibacterial treatment, a PG I value in the blood and a PG II value in the blood were measured in order to calculate a PG I/PG II (pepsinogen I/pepsinogen II) ratio. Using these values, it was calculated how much the values one month after the treatment have changed compared with the values before the eradicating treatment.

Formula for Calculating a Change in the Pepsinogen I/Pepsinogen II Ratio.

Change (%) in the pepsinogen I/pepsinogen II ratio=[(pepsinogen I/pepsinogen II ratio after treatment)−(pepsinogen I/pepsinogen II treatment before treatment)]/(pepsinogen I/pepsinogen II ratio before treatment)×100

The success or failure of the eradication based on the above-mentioned various examinations was studied. Rates of changes in the serum gastrin, serum pepsinogen I, serum pepsinogen II and serum pepsinogen I/pepsinogen II ratio were studied before and after the treatment. The results were shown in, for example, FIG. 7. For the purpose of convenience in FIG. 7, a cut-off value of ±0% was tentatively applied for the serum gastrin and serum pepsinogen I, the cut-off value of −20% was tentatively applied for the serum pepsinogen II, the cut-off value of ±25% was tentatively applied for the serum pepsinogen I/pepsinogen II ratio, the eradication was judged based on these cut-off values, and the accuracy judgment was evaluated. It will be understood that the sensitivity judging the eradication is very good as considered from a change in the serum pepsinogen I/pepsinogen II ratio. Even in validity of judgment inclusive of the eradication and non-eradication, it will be understood that excellent results are obtained from the serum pepsinogen I/pepsinogen II ratio. It was further studied how much the PG I/PG II ratios in the blood have changed compared with the values before the eradicating treatment depending upon success or failure of eradication.

Figure 1:
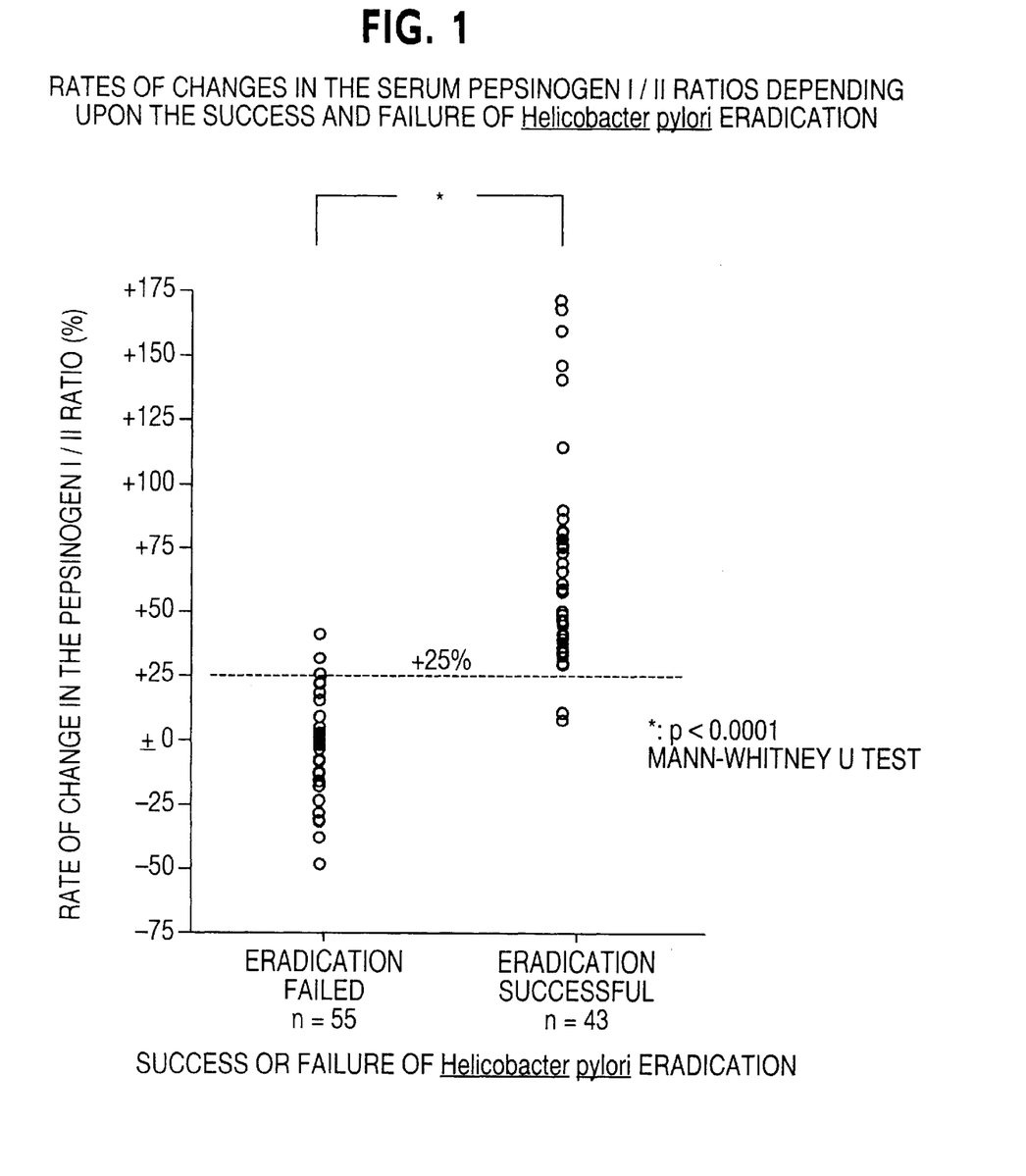
FIG. 1 is a diagram of distribution of rates of changes in the PG I/PG II ratio in the blood before and after the *H. pylori* eradicating treatment depending upon the success and failure of the *H. pylori* eradicating treatment.
Figure 2:
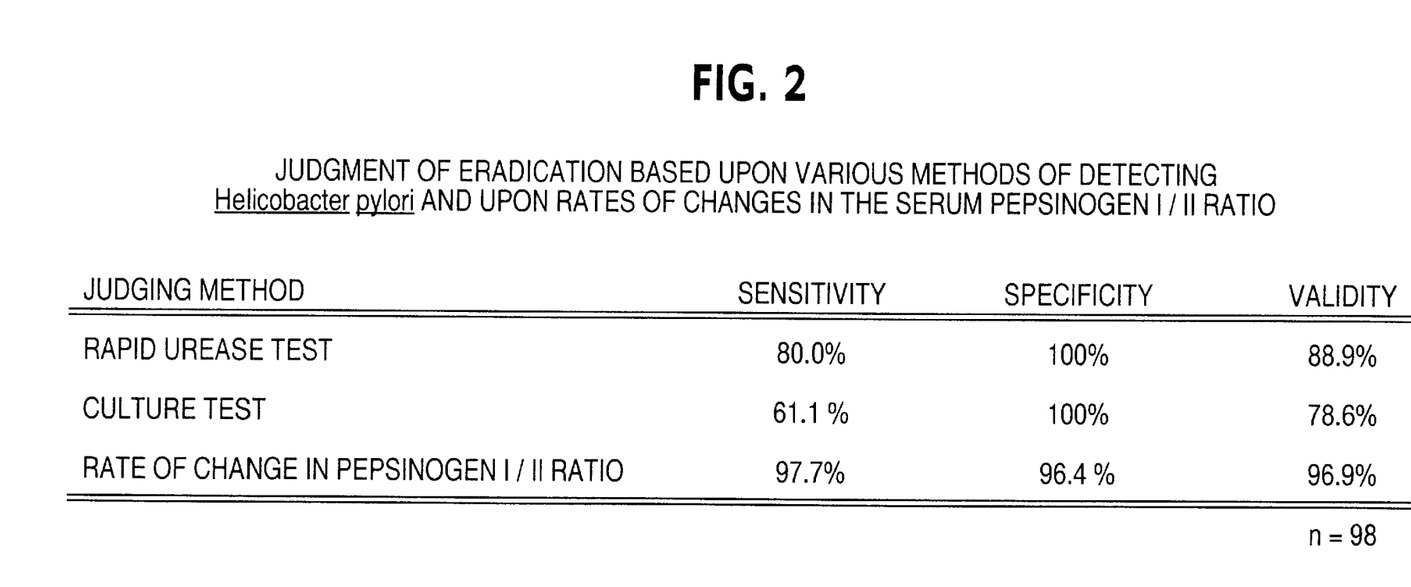
FIG. 2 illustrates sensitivity and specificity in a method of judging eradication based upon rates of changes in the PG I/PG II ratio in the blood before and after the eradicating treatment, featuring superior sensitivity to those of the conventional culture test and rapid urease test.

FIG. 1 shows the results thereof. It was learned that rates of changes in the PG I/PG II ratios in the blood of eradicated group significantly differed from those of the non-eradicated group. It was then learned that this difference could be used as means for judging the eradication of *H. pylori*. A further study indicated that as the PG I/PG II ratio in the blood before the eradication increased, changes in the PG I/PG II ratio in the blood distributed characteristically between the eradicated group and the non-eradicated group. By utilizing this relationship, therefore, changes in the PG I/PG II ratio in the blood before and after the eradication were found to be correlated in reverse proportion to the PG I/PG II ratio in the blood of before the eradication therapy. With reference to this correlation, a predetermined value set according to the values before the treatment was, therefore, found to be able to judge correctly whether the eradication of *H. pylori* was successful or not.

In view of the principle of the present invention, there can be used, as samples, the body fluids such as blood, e.g., whole blood, serum, blood plasma, as well as urine, saliva, abdominal dropsy, gastric juice, exudate of tissue, culture solution of biopsied tissue, and culture solution of cells derived from a living body.

The method of the present invention makes it possible to correctly and reliably judge whether *H. pylori* is eradicated or not without affected by variations among values obtained from the individual patients. That is, it is allowed to judge whether *H. pylori* bacteria are existing or not.

EXAMPLES

The present invention will now be described more concretely by way of the following Examples. Here, however, it should be noted that the invention is in no way limited to these Examples only but can be put into practice even in a variety of other forms without departing from the spirit and scope of the invention.

Example 1

(1) Examination Requiring Endoscopic Examination.

A. Bacterial Culture.

*H. pylori* bacteria were cultured from the gastric mucosal tissues obtained by biopsy during gastroduodenoscopy. The bacteria grew at a very slow rate and its judgment was rendered after the cultivation at 37° C. for about 72 hours by using a skirrow blood agar medium. *H. pylori* bacteria are anaerobic and their culture requires a special device for adjusting the oxygen concentration to 5%. The culture requires controlling the oxygen concentration and a failure to control the oxygen concentration results in a drop in the rate of detecting the bacteria. The bacteria were cultured while making sure the gas concentration by using an oxygen concentration monitor.

B. Rapid Urease Test (RUT).

This is to estimate the presence of *H. pylori* bacteria by utilizing its strong urease activity. The gastric mucosa obtained by biopsy during gastroduodenoscopy was inoculated into a reagent which contained urea and a pH-indicator (e.g., phenol red, red cabbage pigment), and a change in the color was observed. If there is exhibited urease activity of *H. pylori*, urea in the reagent is decomposed to evolve ammonia, whereby the hue of the pH-indicator changes (i.e., the hue changes from, for example, yellow into red).

C. Histopathological Examination.

Gastric mucosa obtained by biopsy during gastroduodenoscopy was specially stained to make sure the presence or absence of *H. pylori* bacteria using a microscope. Special staining can be accomplished by staining the gastric mucosal sections with Warthin-Starry stain and observing it using an optical microscope, staining the section with acridine orange and observing it using a fluorescent microscope, or staining the gastric mucosa with Giemsa stain.

D. Competitive PCR Method.

In compliance with Nippon Shokakibyo Gakkai Zasshi (Jap. J. Gastroenterol), Vol. 90 (No. 11), 1993, p. 2962, *H. pylori* bacteria in gastric mucus were quantitatively detected by a competitive PCR method (hereinafter referred to as cPCR method). DNAs were synthesized for obtaining the following primers and the competitors. Base sequences of the primers were extended to 21 bp to enhance specificity.

Primers

HPU18N: 5'-CCCATTTGACTCAATGCGATG-3' (SEQ ID No:1)

HPU54N: 5'-TGGGATTAGCGAGTATOTCGG-3' (SEQ ID No:2)

Competitor sDNA: 5'-CCCATTTGACTCAATGCGATGCCCG-CCTTTGATGATCATGTTGGG CCGACAT-ACTCGCTAATC CCA-3' (SEQ ID No: 3)

Gastric juice was collected by suction during gastroduodenoscopy. The gastric juice collected by suction was subjected to the centrifuge, DNAs were extracted from 100 µl of the precipitated mucus by using a DNA extraction kit in the market, and the extracted DNAs were dissolved in 400 µl of TE which was then used as an *H. pylori* DNA solution.

The reaction solution of the cPCR method possessed a composition, per a reaction tube, of 4.00 µl of dNTPs (2.5 mM each), 5.00 µl of 10×PCR buffer solution, 0.25 µl of Taq DNA polymerase (5U/µl), 0.50, µl of primer (HPU18N and HPU54N: 50 mol/µl each), 5.00 µl of *H. pylori* DNA solution, and 4.0 μl of a competitor of various concentrations (sDNA: $1.0 \times 5^0$ to $1.0 \times 5^{-8}$ pg/μl) and being added with the water so that the total volume was 50 μl. The solution was subjected to PCR. PCR amplification is consisted of initial denaturation of target DNA at 95° C. for 5 min. followed by denaturation at 94° C. for 1 min., primer annealing at 55° C. for 1 min., and extension at 72° C. for 1 min. The final cycle included extension for 8 min. at 72° C. to ensure full extension of the products. Samples were amplified 25 to 40 consecutive cycles.

The PCR products were analyzed by electrophoresis, and the concentrations of 132 bp bands of *H. pylori* DNA and the concentration of 66 bp bands of competitor were measured by a densitometer. A point was found at which the concentration of the 132 bp band became equal to the concentration of the 66 bp band, in order to calculate the amount of *H. pylori* in the gastric mucus. The case where the amount of *H. pylori* was greater than $10^4/100$ μl was regarded to be positive. The case where the 132 bp bands was not recognized but the 66 bp bands was recognized was regarded to be negative. When the amount of *H. pylori* was not larger than $10^4/100$ μl, the judgment was not rendered since it might have been contaminated. This helps decrease false positive caused by contamination. When neither the 132 bp bands nor the 66 bp bands is recognized, the PCR reaction was thought to be incomplete and the judgment was not rendered. It is therefore considered that false negative due to poor PCR is eliminated. When the judgment could not be rendered, other examinations were relied upon (culture, rapid urease test, histology, etc.).

(2) Measurement of PG I Value and PG It Value in the Blood.

The PG I value and PG II value in the blood were measured by using monoclonal antibodies specific to PG I and PG II, i.e., by using pepsinogen I RIA BEAD and pepsinogen II RIA BEAD (manufactured by Dainabot Co., ltd.) as a solid-phase antibody and a label antibody.

First, a reaction mixture consisting of a sample and a standard PG I sample or a standard PG II sample each in an amount of 25 μl, an anti-PG I antibody bead or an anti-PG II antibody bead, and 200 μl of a $^{125}$I-labelled anti-PG I antibody or anti-PG II antibody, was subjected to the shaking incubation treatment at room temperature for three hours. The reaction solution was sucked, washed, rinsed with distilled water three times and, finally, a radioactivity of the bead was measured.

The PG I value and PG II value in the blood are also measured according to the method disclosed in Samloff TM: "Pepsinogens I and II, purification from gastric mucosa and radioimmunoassay in serum", Gastroenterology, 82: 26–33, 1982.

(3) Consideration of Results of PG I Value and PG II Value in the Blood Depending Upon Success or Failure of Eradication.

Ninety-eight patients suffering from peptic ulcer disease (48 cases of gastric ulcer; average age 59±11 and 50 cases of duodenal ulcer; average age 49±13) were eradication-treated:
i.e., ① 27 cases-in which lansoprazole (30 mg/day, 6 to 8 weeks) alone was administered;

② 32 cases in which lansoprazole (30 mg/day, 6 to 8 weeks) and amoxicillin (2 g/day, two weeks) were administered;

③ 21 cases in which lansoprazole (30 mg/day, 6 to 8 weeks), amoxicillin (2 g/day, two weeks) and metronidazole (1000 mg/day, two weeks) were administered;

④ 3 cases in which lansoprazole (30 mg/day, 6 to 8 weeks), clarithromycin (800 mg/day, two weeks) and metronidazole (1000 mg/day, two weeks) were administered; and ⑤ 5 cases in which ranitidine (300 mg/day, two weeks) alone was administered.

The PG I value and PG II value in the blood were measured before and after the treatment. The results of the blood samples within one to three months after the administration (eradication) has been finished were divided by values before the eradicating treatment and were expressed in terms of percentage to compare them together with the success or failure of eradication. The results of examination such as culture test, rapid urease test, PCR method, and ammonia in gastric juice/urea in gastric juice ratio measurement, were compared and discussed, and only the case in which all of them were negative was judged to be eradication successful. As a result, eradication was recognized in 43 cases among 98 cases.

The judgment of whether the sample has been eradicated or not was achieved depending on a cut-off value. When the cut-off value was +25%, the sensitivity of eradication judgment was 95.3% and the specificity was 94.5% (FIG. 1).

After one month has passed from the end of the eradicating treatment by the culture test method that has heretofore been carried out, the sensitivity and specificity were 61.1% and 100%, respectively. In the urease test, they were 80.0% and 100%, respectively, from which it was recognized that the detection sensitivity drops after the eradicating treatment.

Figure 3:
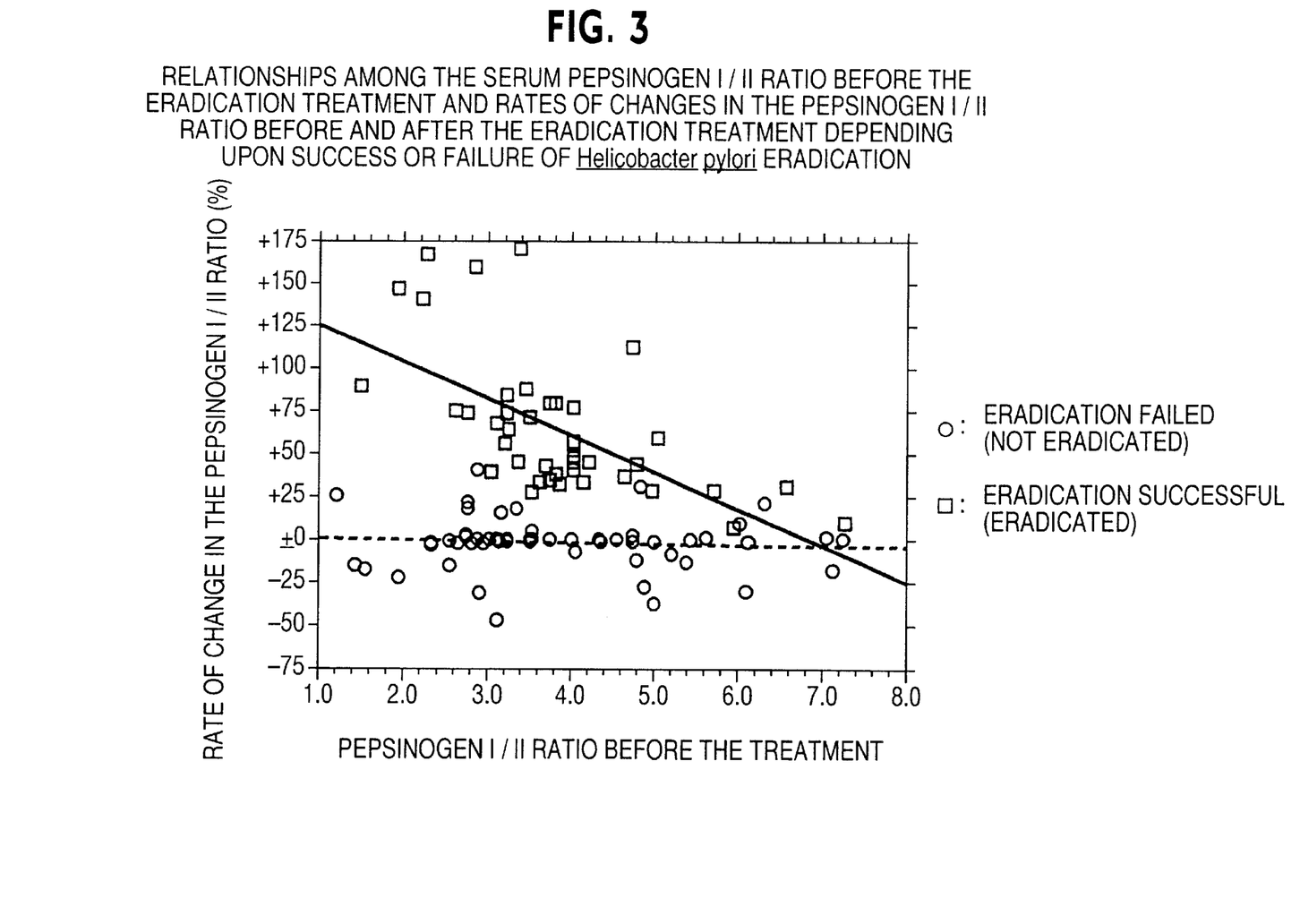
FIG. 3 is a diagram illustrating relationships among the PG I/PG II ratio in the blood before the eradicating treatment, rates of changes in the PG I/PG II ratio in the blood before and after the eradicating treatment depending upon success and failure of eradication.

Concerning the cases that were judged to be eradicated or not eradicated, the PG I/PG II ratios before the eradicating treatment were plotted along the abscissa, and rates of changes in the PG I/PG II ratio in the blood calculated in accordance with the aforementioned formula 1 were plotted along the ordinate. It was then recognized that, when eradicated, the PG I/PG II ratio in the blood changed more greatly, as PG I/PC II ratios before the eradicating treatment that had been judged to be exhibiting basal PG I/PG II ratios were smaller. in the group having high PG I/PG II ratios before the eradicating treatment, rates of changes in the PG I/PG II ratio in the blood were smaller. In the group without eradication, rates of changes were almost 0% irrespective of the values of the PG I/PG II ratios before the eradicating treatment.

Therefore, by not simply setting a fixed (or universal) cut-off value to a rate of the change in the PG I/PG II ratio in the blood and instead setting a non-fixed cut-off value which is inversely (or reversely) to the value of the basal PG I/PG II ratio, it becomes possible to render more correct eradication judgment (FIG. 3). For instance, a cut-off value for the rate of change in the PG I/PG II ratio in the blood is tentatively set to be +40% when the PG I/PG II ratio in the blood is not larger than 3, the cut-off value for the rate of change in the PG I/PG II ratio in the blood is tentatively set to be +25% when the PG I/PG II ratio in the blood is not smaller than 3 but is not larger than 5, and the cut-off value for the rate of change in the PG I/PG II ratio in the blood is tentatively set to be about +10% when the PG I/PG II ratio in the blood is not smaller than 5, in order to more correctly judge whether the eradication is successful or not.

FIG. 3 illustrates a relationship between the PG I/PG II ratios of before the eradicating treatment and rates of the changes in the PG I/PG II ratios before and after the eradicating treatment depending upon the success or failure of *H, pylori* eradication, wherein a solid line represents a regression line of the group with eradication and a dotted line represents a regression line of the group without eradication. In the group with eradication, a significant correlation was recognized (r=0.61, p<0.0001) between the PG I/PG II ratios before the treatment and rates of the change in the PG I/PG II ratios before and after the treatment. In the group without eradication, rates of changes before and after the treatment were almost 0%, no significant changes were recognized, and no correlation was recognized between the pre-treatment values and rates of changes before and after the treatment, either (r=0.063, p=0.65).

In the eradicated group, rates of changes in the PG I/PG II ratio in the blood did not vary among the method of eradicating treatment.

Example 2

Figure 4:
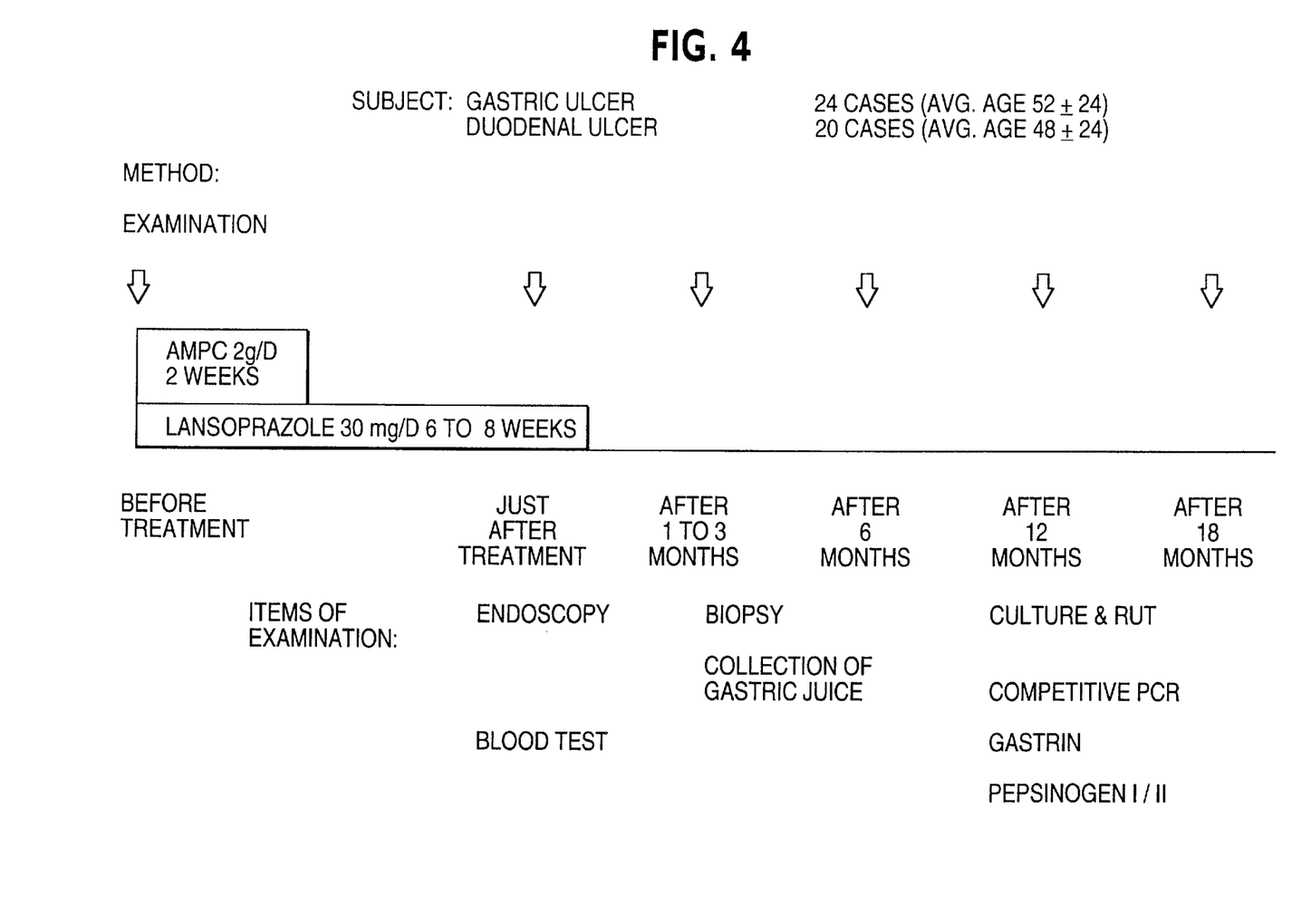
FIG. 4 is a diagram illustrating schedules of various examinations for an *H. pylori*-infected patient before and after the eradicating treatment.
Figure 5A:
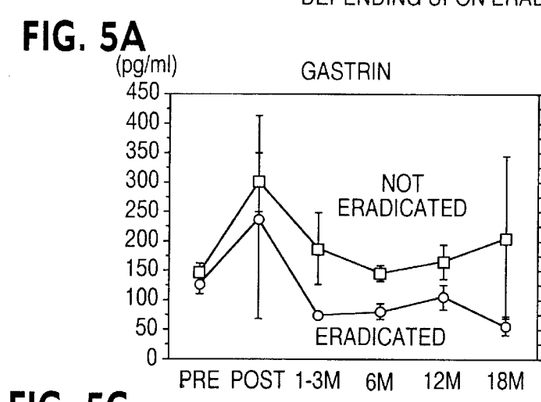
FIG. 5 is a diagram illustrating transitions in the serum gastrin value and serum pepsinogen value depending upon the eradication and non-eradication.
Figure 5B:
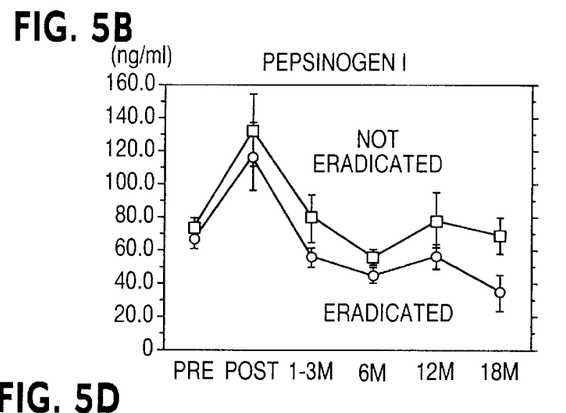
Figure 5C:
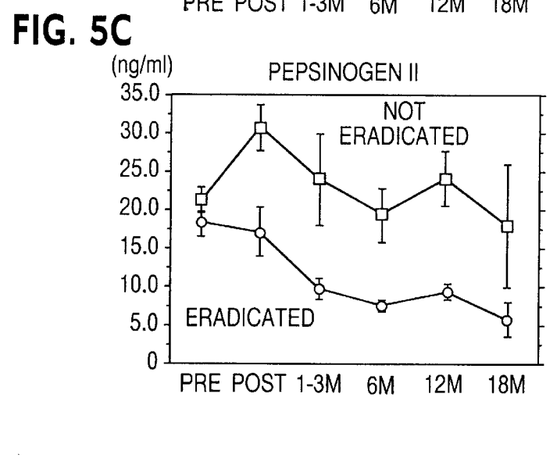
Figure 5D:
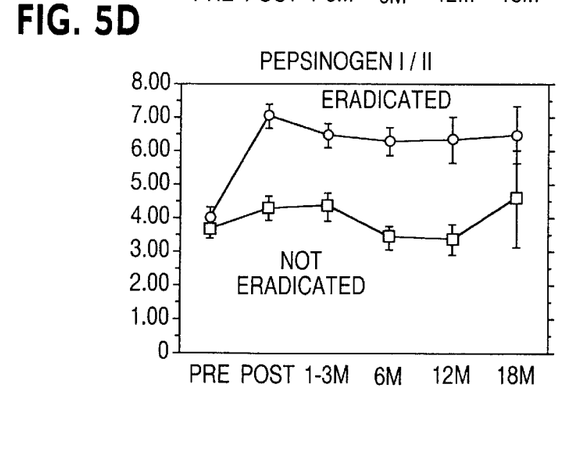
Figure 6A:
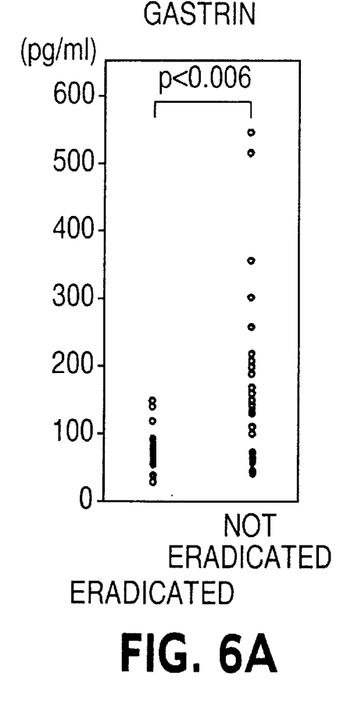
FIG. 6 is a diagram illustrating distribution of the the serum gastrin and serum pepsinogen values after the eradicating treatment depending upon the eradication and non-eradication.
Figure 6B:
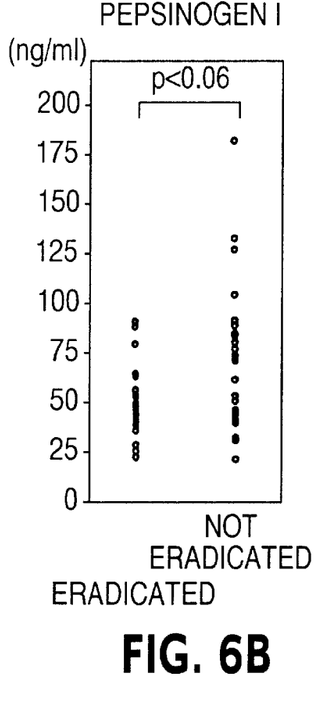
Figure 6C:
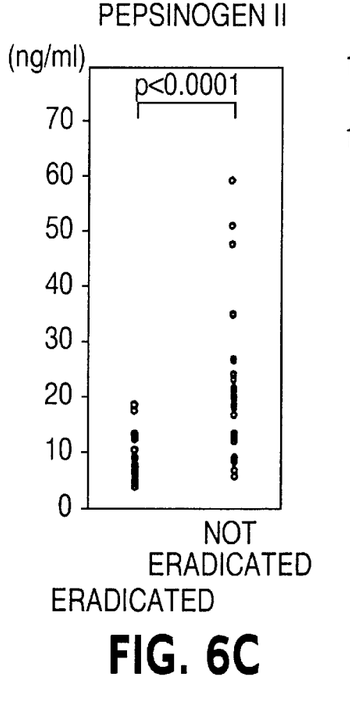
Figure 6D:
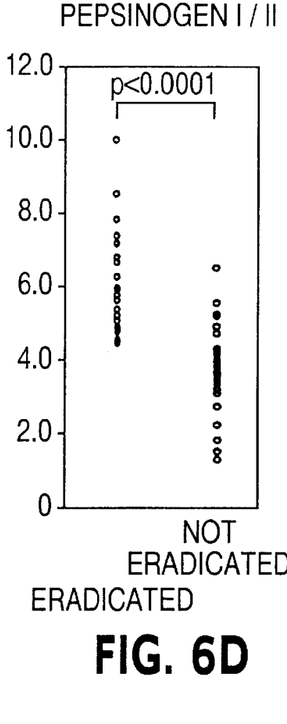
Figure 7A:
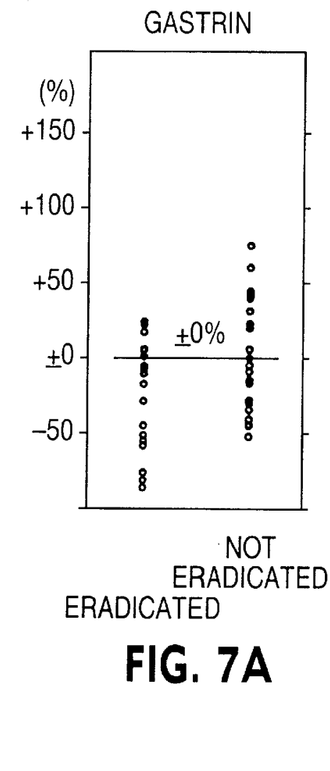
FIG. 7 is a diagram illustrating rates of changes in the serum gastrin and serum pepsinogen depending upon the eradication and non-eradication.
Figure 7B:
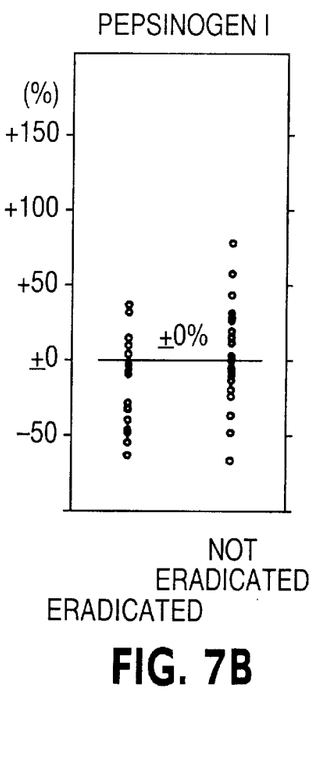
Figure 7C:
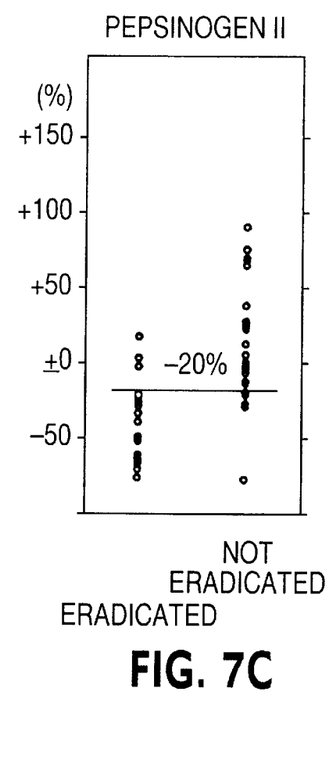
Figure 7D:
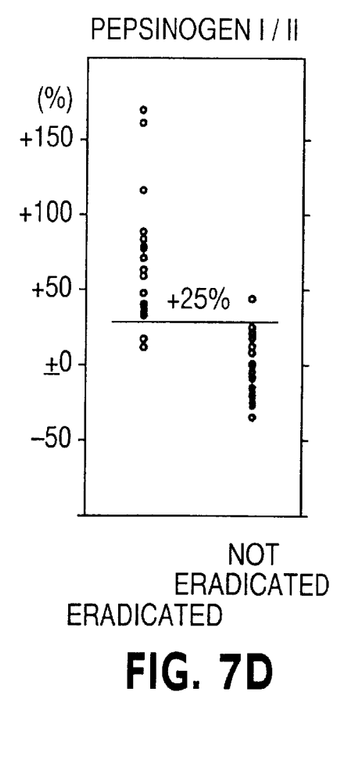

Lansoprazole and antibiotic were administered as explained in Example 1 to patients (24 cases of gastric ulcer and 20 cases of duodenal ulcer) who were confirmed to have been infected with *H. pylori* by culture test, urease test and a PCR method as explained in Example 1. After the administration is finished, the blood was examined (gastrin, pepsinogen I, pepsinogen II) as shown in FIG. 4. After more than a month has passed from the administration of the therapeutic drugs, the endoscopy was conducted and *H. pylori* was examined by the urease test, culture test, and a competitive PCR method. Only in the case where all of them were negative, it was judged that the eradication was successful. The eradication was recognized in 24 cases among 44 cases.

FIG. 5 illustrates transition in the blood test (gastrin, pepsinogen I, pepsinogen II) and pepsinogen I/pepsinogen II ratio before and after the treatment. It was learned that nearly constant values were maintained one month after the eradicating treatment, and different values were maintained depending upon whether the eradication was successful or not. Therefore, values were compared and discussed before the treatment and one to three months after the treatment.

FIG. 6 shows distribution of serum gastrin, serum pepsinogen I, serum pepsinogen II, and serum pepsinogen I/pepsinogen II ratio during the treatment depending upon is whether the eradication was successful or not. In all of them, significant differences were recognized between the group with eradication and the group without eradication. These cases, however, include different diseases such as duodenal ulcer and gastric ulcer. Besides, in the individual cases, the values before the treatment are varying and are, often, overlapping. Besides, it is difficult to judge whether the eradication was successful or not depending upon the blood gastrin value and the blood pepsinogen values obtained in the individual cases, Accordingly, the individual cases were studied in regard to how much (%) the values after the treatment have changed compared with the values before the treatment.

FIG. 7 illustrates rates of changes in the blood gastrin, blood pepsinogen I, blood pepsinogen II, and blood pepsinogen I/pepsinogen II ratio before and after the treatment. For the purpose of convenience referring to FIG. 7, the cut-off value of ±0% was tentatively applied for the blood gastrin and blood pepsinogen I, the cut-off value of −20% was tentatively applied for the blood serum pepsinogen II, and the cut-off value of +25% was tentatively applied for the blood pepsinogen I/pepsinogen II ratio, and the eradication was judged based upon the cut-off values to evaluate the accuracy of diagnosis. The sensitivity of diagnosis of eradication was as very good as 94.7% based upon the rates of changes in the blood pepsinogen I/pepsinogen II ratio. Even the validity inclusive of the eradication and non-eradication was as high as 93.2% based upon the serum pepainogen I/pepsinogen II ratio.

Table 1 shows accuracy of various methods of judging *H. pylori* eradication based upon the PCR method.

TABLE 1

Accuracy of various eradication judging methods based upon the PCR method.

| Eradication Judging Method | Sensitivity | Specificity | Validity |
|---|---|---|---|
| Culture | 69.2% | 100% | 78.4% |
| Rapid Urease Test (RUT) | 79.2% | 100% | 87.8% |
| Culture & urease test | 86.4% | 100% | 92.7% |
| change rate in gastrin | 55.5% | 70.6% | 61.4% |
| Change rate in pepsinogen I | 61.5% | 72.2% | 63.6% |
| Change rate in pepsinogen II | 85.0% | 87.5% | 86.4% |
| Change rate in pepsinogen I/II | 94.7% | 92.0% | 93.2% |
| Culture & RUT & Change rate in pepsinogen I/II | 100% | 95.5% | 97.5% |

Sensitivity: (No. of judging eradicated samples by the instant method/No. of true eradicated samples)×100

Specificity: (No. of judging non-eradicated samples by the instant method/No. of true non-eradicated samples)×100

Validity: (No. of judging eradicated samples by the instant method+No. of judging non-eradicated samples by the instant method)/(NO. of true eradicated samples+No. of true non-eradicated samples)×100

When the eradication of *H. pylori* is judged by adding the pepsinogen I/pepsinogen II ratio to the RUT and culture test, the sensitivity is accomplished 100%. This manifests that the eradication of *H. pylori* is judged excellently based upon the combination of bacteriological testing and serum diagnosis. Moreover, the validity is as high as 97.5%.

The method of the present invention makes it possible to relatively correctly judge the eradication without conducting endoscopy. Besides, this method which does not require endoscopy causes the person to be tested to bear a reduced burden, making it possible to conduct examination and measurement a plural times repetitively. Moreover, pepsinogen I in the body fluid such as pepsinogen I in the blood and pepsinogen II in the body fluid such as pepsinogen II in the blood, can be measured by using testing reagents that are in the market, enabling the measurement to be taken easily and quickly. Accordingly, there is no need of developing or buying new equipment, and no special skill or technique is required, either.

What is claimed is:

1. A method for judging the eradication of *H. pylori* in a patient after the patient has been administered a treatment for eradication, which comprises:
   (1) measuring a PG I value and a PG II value in a body fluid of an *H. pylori* positive patient (a) before treatment for eradication of *H. pylori* and (b) after treatment for eradication of *H. pylori*,
   (2) determining a PG I/PG II ratio in the body fluid sample before the treatment for eradication and a PG I/PG II ratio in the body fluid sample after the treatment for eradication,
   (3) determining a rate of change of (i) the body fluid PG I/PG II ratio before the treatment for eradication to (ii) the body fluid PG I/PG II ratio after the treatment for eradication, and
   (4) using said rate of change in the body fluid PG I/PG II ratios as a marker of eradication of *H. pylori*, by selecting a cut-off point for said rate of change of the body fluid PG I/PG II ratios which is based upon the value of the body fluid PG I/PG II ratio before the treatment for eradication of *H. pylori*, and
      wherein said cut-off point for said rate of change in body fluid is set inversely proportional to the value of the body fluid PG I/PG II ratio before the treatment for eradication of *H. pylori*,
      wherein when said rate of change in body fluid PG I/PG II ratio is greater than the cut-off point, *H. pylori* is judged to be eradicated, and
      wherein when said rate of change in body fluid PG I/PG II ratio is not greater than the cut-off point, *H. pylori* is judged to be not eradicated.

2. A method for measuring and judging whether *H. pylori* is remaining or not in a patient after the patient has been administered a treatment for eradication, which comprises:
   (1) measuring a PG I value and a PG II value in a body fluid sample (a) before treatment for eradication of *H. pylori* and (b) after treatment for eradication of *H. pylori*,
   (2) determining a PG I/PG II ratio in the body fluid sample before the treatment for eradication and a PG I/PG II ratio in the body fluid sample after the treatment for eradication,
   (3) determining a rate of change of (i) the body fluid PG I/PG II ratio before the treatment of eradication to (ii) the body fluid PG I/PG II ratio after the treatment for eradication, and
   (4) using said rate of change in the body fluid PG I/PG II ratios as a marker of eradication of *H. pylori*, by selecting a cut-off point for said rate of change of the body fluid PG I/PG II ratios which is based upon the value of the body fluid PG I/PG II ratio before the treatment for eradication of *H. pylori*, and
      wherein said cut-off point for said rate of change in body fluid is set inversely proportional to the value of the body fluid PG I/PG II ratio before the treatment for eradication of *H. pylori*,
      wherein when said rate of change in body fluid PG I/PG II ratio is greater than the cut-off point, *H. pylori* is judged to be eradicated, and
      wherein when said rate of change in body fluid PG I/PG II ratio is not greater than the cut-off point, *H. pylori* is judged to be not eradicated.

3. The method according to claim 1 or 2, wherein the PG I vale and the PG II value in the body fluid samples are measured by using an immunologically measuring reagent which comprises a monoclonal antibody.

4. The method according to claim 3, wherein the monoclonal antibody is an anti-pepsinogen I monoclonal antibody or an nti-pepsinogen II monoclonal antibody.

5. The method according to claim 1 or 2, wherein the cut-of point is set to be +40% when the body fluid PG I/PG II ratio n the sample before the treatment for eradication of *H. pylori* is not greater than 3.

6. The method according to claim 1 or 2, wherein the cut-of point is set to be +25% when the body fluid PG I/PG II ratio in the sample before the treatment for eradication of *H. pylori* is greater than 3 but not greater than 5.

7. The method according to claim 1 or 2, wherein the cut-of point is set to be +10% when the body fluid PG I/PG II ratio in the sample before the treatment for eradication of *H. pylori* is greater than 5.

8. The method according to claim 1 or 2, wherein the body fluid sample is a blood sample.

9. The method according to claim 8, wherein the blood sample is serum, blood plasma or whole blood.

* * * * *

SEQUENCE LISTING

<160> NUMBER OF SEQ ID NOS: 3

<210> SEQ ID NO 1
<211> LENGTH: 21
<212> TYPE: DNA

```
-continued

<213> ORGANISM: Artificial Sequence
<220> FEATURE:
<223> OTHER INFORMATION: Description of Artificial Sequence: Synthetic
      DNA Primer

<400> SEQUENCE: 1
cccatttgac tcaatgcgat g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 2
tgggattagc gagtatgtcg g                                              21

<210> SEQ ID NO 3
<211> LENGTH: 66
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cccatttgac tcaatgcgat gcccgccttt gatgatcatg ttgggccgac atactcgcta    60
atccca                                                               66
```